(12) United States Patent
Yamakawa et al.

(10) Patent No.: US 9,039,602 B2
(45) Date of Patent: May 26, 2015

(54) ENDOSCOPE PROPELLING DEVICE

(75) Inventors: Shinichi Yamakawa, Kanagawa (JP);
Tsuyoshi Ashida, Kanagawa (JP);
Takayuki Nakamura, Kanagawa (JP);
Yasunori Ohta, Kanagawa (JP);
Charles Alan Brantingham, St. Paul, MN (US)

(73) Assignee: FUJIFILM Corporation, Tokyo (JP)

( * ) Notice: Subject to any disclaimer, the term of this patent is extended or adjusted under 35 U.S.C. 154(b) by 337 days.

(21) Appl. No.: 13/538,427

(22) Filed: Jun. 29, 2012

(65) Prior Publication Data
US 2013/0006053 A1 Jan. 3, 2013

Related U.S. Application Data

(60) Provisional application No. 61/503,987, filed on Jul. 1, 2011.

(51) Int. Cl.
*A61B 1/00* (2006.01)
(52) U.S. Cl.
CPC .................... *A61B 1/0016* (2013.01)
(58) Field of Classification Search
CPC .......................... A61B 1/0016; A61B 1/00156
USPC .......................... 600/114, 115, 127, 104, 106
See application file for complete search history.

(56) References Cited

U.S. PATENT DOCUMENTS

| 5,181,888 | A | * | 1/1993 | Takahashi et al. | ............ 474/101 |
| 7,736,300 | B2 | | 6/2010 | Ziegler et al. | |
| 2008/0045790 | A1 | * | 2/2008 | Ziegler et al. | ................. 600/114 |
| 2011/0265275 | A1 | * | 11/2011 | Allen et al. | ................. 15/104.05 |

FOREIGN PATENT DOCUMENTS

| JP | 2005-253892 A | 9/2005 |
| JP | 2009-513250 A | 4/2009 |

* cited by examiner

*Primary Examiner* — Anhtuan T Nguyen
*Assistant Examiner* — Rynae Boler
(74) *Attorney, Agent, or Firm* — Birch, Stewart, Kolasch & Birch, LLP

(57) ABSTRACT

A propelling device includes a traveling body that rotates in a state of being brought into contact with an inner wall of an alimentary canal, an external cylinder around which the traveling body is wound, and a mounting cylinder on which a tip end portion of an endoscope is mounted. Three driven rollers are rotatably attached to the external cylinder. The traveling body is pinched between the driven rollers and driving gears. As the driving gears rotate, the traveling body travels in a circulating manner. A rotating shaft of the driven roller located at the center among the three driven rollers is held by a shaft hole that is made long in a gear arrangement direction in which the driving gears are disposed side by side.

10 Claims, 9 Drawing Sheets

ENDOSCOPE PROPELLING DEVICE

CROSS REFERENCE TO RELATED APPLICATIONS

This nonprovisional application claims the benefit of U.S. Provisional Application No. 61/503,987 filed on Jul 1, 2011. The entire contents of the above application is hereby incorporated by reference.

BACKGROUND OF THE INVENTION

1. Field of the Invention

The present invention relates to a propelling device for assisting insertion of a tip end portion of an endoscope.

2. Description of the Related Art

Endoscopes are widely used for examination of curved alimentary canals like the large intestine or the small intestine. The endoscopes are constituted by a manipulating part and a flexible insertion part. The insertion part is inserted into an alimentary canal. Observation, diagnosis and medical treatment of the inner wall surface of an alimentary canal are performed (for example, refer to JP 2005-253892 A). In this case, if the alimentary canal is a sigmoid colon that is curved in a complicated manner and moves relatively freely, a high level of skill is required to advance the insertion part to the depths of the sigmoid colon. For this reason, an endoscope whose insertion part can be easily advanced to the depths even within an alimentary canal, such as the sigmoid colon which is curved intricately, is needed.

In recent years, a propelling device, which is attached to the tip end side of the insertion part and propels the insertion part within an alimentary canal has been developed (for example, refer to JP 2009-513250 A). A traveling body (circulating moving body) of this propelling device is attached to an external cylinder mounted on the tip end side of the insertion part, and the traveling body is made to travel in a circulating manner in a state where an outside of the traveling body is brought into contact with the inner wall of the alimentary canal, and thereby the tip end side of the insertion part is moved within alimentary canal by the friction generated between the outside of the traveling body and the inner wall of the alimentary canal. In this propelling device, the traveling body is pressed against a driving gear and pinched by a pair of driven rollers, and the driving gear is rotated with a driving force from the outside, whereby the rotation of the driving gear is transmitted to the traveling body to make the traveling body travel. There is also described an another configuration in which a plurality of driving sets each including a pair of driven rollers and a driving gear are provided side by side in the traveling direction of the traveling body such that the traveling body is made to travel.

One technique for transmitting a large driving force to the traveling body is to increase the contact area between the driving gear and the traveling body. Accordingly, it is useful to increase the number of the driving gears by providing a plurality of driving sets side by side in the traveling direction of the traveling body as described in JP 2009-513250 A. However, on the other hand, since a pair of driven rollers are needed for every driving gear, a problem occurs in that the total length of the propelling device becomes large.

Thus, the number of the driven rollers can be reduced by arranging two driving gears in proximity with each other, and arranging one driven roller so as to face a portion between the driving gears, such that the traveling body is pinched between the one driven roller and two driving gears. However, in the case of adopting such a configuration, there is a concern that due to an assembling error of the driving gears and the driven roller, respective gaps between the respective driving gears and the driven roller may become non-uniform, and as a result, the respective pinching forces may become non-uniform. If the respective pinching forces become non-uniform, not only a driving force is no longer transmitted to the traveling body effectively, but also tensioning or loosening occurs on the traveling body between the respective driving gears, which causes a problem that the traveling body, the driving gears, the driven roller, and the like are damaged.

SUMMARY OF THE INVENTION

An object of the present invention is to provide a propelling device capable of preventing non-uniformity of pinching forces between a driven roller and respective driving gears.

In order to achieve the above object, the propelling device of the present invention includes a mounting cylinder, an external cylinder, a traveling body, two driving gears, a first driven roller, and one set of first shaft holes. The mounting cylinder fits into an insertion part of an endoscope. The external cylinder is disposed at an outer periphery of the mounting cylinder. The traveling body is wound around the external cylinder, and moves from an inside of the external cylinder to an outside thereof and returns to the inside again so as to travel in a circulating manner. The two driving gears rotate by receiving a driving force from a driving source. The two driving gears are disposed so as to push the traveling body from the inside of the external cylinder. The two driving gears are disposed side by side with their rotating shafts parallel to each other in a direction in which the traveling body is made to travel. The first driven roller is rotatably provided to the external cylinder so as to face a portion between the two driving gears. The rotating shaft of the first driven roller is made parallel to the rotating shafts of the driving gears. The first driven roller pinches the traveling body between the first driven roller and the respective driving gears to transmit the rotation of the respective driving gears to the traveling body. The one set of first shaft holes holds each end of the rotating shaft of the first driven roller. Each of the first shaft holes is formed to be long in a gear arrangement direction in which the two driving gears are disposed side by side, such that the first driven roller is held by the first shaft holes so as to be movable in the gear arrangement direction.

Preferably, the propelling device further includes two second driven rollers. The two second driven rollers are disposed side by side in the gear arrangement direction so as to sandwich the first driven roller, and pinch the traveling body between the second driven rollers and the driving gears.

A roller unit has the first driven roller, the second driven rollers, a pair of holding members, and an attachment member. The pair of holding members is disposed at each side of the first driven roller and the second driven rollers. Each of the holding members is formed with the first shaft hole and second shaft holes for holding ends of the rotating shafts of the two second driven rollers. The attachment member attaches the holding member to the external cylinder such that the holding member is rotatable around a rotating shaft parallel to the first driven roller.

The propelling device preferably includes a rotation cylinder, a worm gear, and a housing cylinder. The rotation cylinder is rotatably disposed at the outer periphery of the mounting cylinder, and is rotated by receiving the driving force from the driving source. The worm gear is formed at an outer peripheral surface of the rotation cylinder, and meshes with the driving gears, such that the driving gears are rotated by the rotation of the rotation cylinder. The housing cylinder is disposed between the rotation cylinder and the external cylinder, and holds the driving gears in a state that the driving gears protrude from an outer peripheral surface of the housing cylinder.

The propelling device preferably includes a mounting cylinder, an external cylinder, a traveling body, N (N is two or more) number of driving gears, (N−1) number of first driven rollers, and (N−1) number of sets of first shaft holes. The mounting cylinder fits into the insertion part of an endoscope. The external cylinder is disposed at the outer periphery of the mounting cylinder. The traveling body moves from an inside of the external cylinder to an outside thereof and returns to the inside again so as to travel in a circulating manner. The traveling body is wound around the external cylinder so as to be made endless. The driving gears rotate by receiving a driving force from the driving source. The N number of the driving gears are disposed closer to the mounting cylinder than the traveling body inside the external cylinder, and the N number of the driving gears are disposed side by side with their rotating shafts parallel to each other in a direction in which the traveling body is made to travel. The (N−1) number of the first driven rollers are rotatably provided at the external cylinder, and each of the (N−1) number of the first driven rollers is disposed to face a portion between the adjoining driving gears. The rotating shaft of each of the (N−1) number of the first driven rollers is made parallel to the rotating shafts of the driving gears, and each of the (N−1) number of the first driven rollers and each of the driving gears pinch the traveling body therebetween to transmit the rotation of each of the driving gears to the traveling body. The (N−1) number of the sets of first shaft holes hold each end of the rotating shafts of the (N−1) number of the first driven rollers. The (N−1) number of the sets of first shaft holes are formed so as to be long in a gear arrangement direction in which the driving gears are disposed side by side such that the (N−1) number of the first driven rollers are held by the (N−1) number of sets of the first shaft holes so as to be movable in the gear arrangement direction.

Preferably, the propelling device includes two second driven rollers for pinching the traveling body between the second driven rollers and the driving gears. The second driven rollers are disposed at each end in the gear arrangement direction so as to sandwich the (N−1) number of the first driven rollers.

Preferably, the traveling body is a tubular bag. The traveling body may be constituted by a plurality of endless belts.

According to the present invention, the first driven roller disposed so as to face a portion between the two driving gears is held by the first shaft holes that are made long in the gear arrangement direction in which the driving gears are disposed side by side. Therefore, the first driven roller freely moves to and is positioned at a position where the gaps between the first driven roller and the respective driving gears become uniform. Thereby, the pinching forces for pinching the traveling body between the first driven roller and the each of the driving gears can be made uniform.

BRIEF DESCRIPTION OF THE DRAWINGS

The above object and advantages can be easily understood by those skilled in the art by reading the detailed description of the preferred embodiments of the present invention with reference to the attached drawings.

DESCRIPTION OF THE PREFERRED EMBODIMENTS

Figure 1:
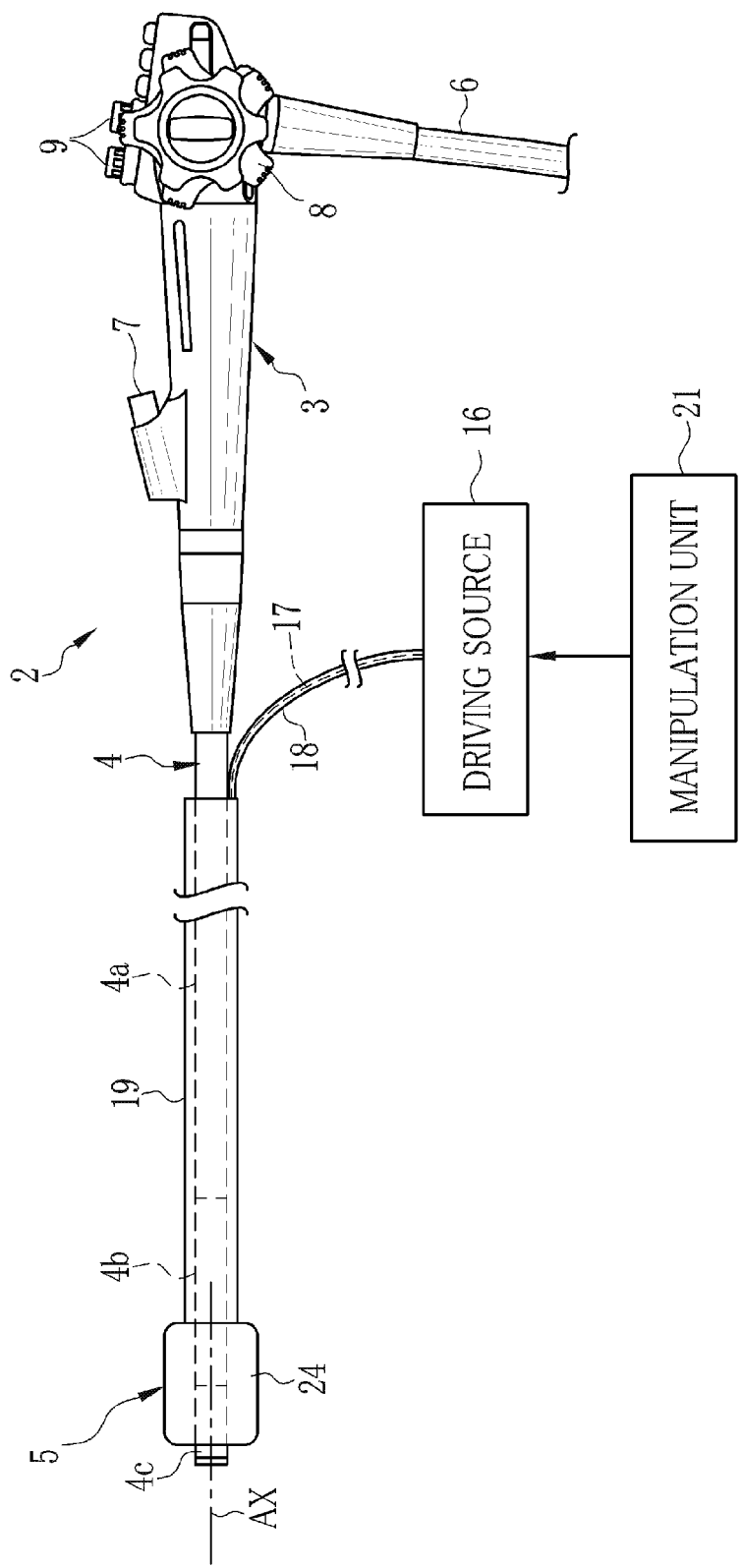
FIG. 1 is a schematic view showing an endoscope mounted with a propelling device.

In FIG. 1, the endoscope 2 includes a manipulating part 3, and an insertion part 4 provided to be continuous with the manipulating part 3 and inserted into body cavities, for example, alimentary canals such as the large intestine. The propelling device 5 assists advancement or retreat of the insertion part 4 within a body cavity, and is mounted on the tip end side of the insertion part 4.

A universal cord 6 for allowing an air/water supply tube, a signal cable, a light guide, and the like to pass therethrough is connected to the manipulating part 3, and a processor device, a light source device, and an air/water supply device (none of which are shown) are connected to the tip end of the universal cord 6. The manipulating part 3 is provided with a forceps entrance 7 that allows treatment tools such as an electric scalpel to be inserted therethrough, angle knobs 8, manipulation buttons 9 used for various manipulations such as air supply, water supply, suction, and the like.

The insertion part 4 includes a flexible tube portion 4a having flexibility, a curving portion 4b capable of being curved in the up-and-down direction and in the right-and-left direction, and a tip end rigid portion 4c, in this order from the side of the manipulating part 3. The flexible tube portion 4a has, for example, a length of 1 to 2 m in order to make the tip end rigid portion 4c arrive at a target position of a tract within the body. The curving portion 4b is curved in the up-and-down direction and the right-and-left direction in conjunction with the manipulation by the angle knobs 8, and thereby the tip end rigid portion 4c can be pointed toward a desired direction. Furthermore, the symbol AX represents an axis of the insertion part 4 (hereinafter referred to as insertion axis).

Figure 2:
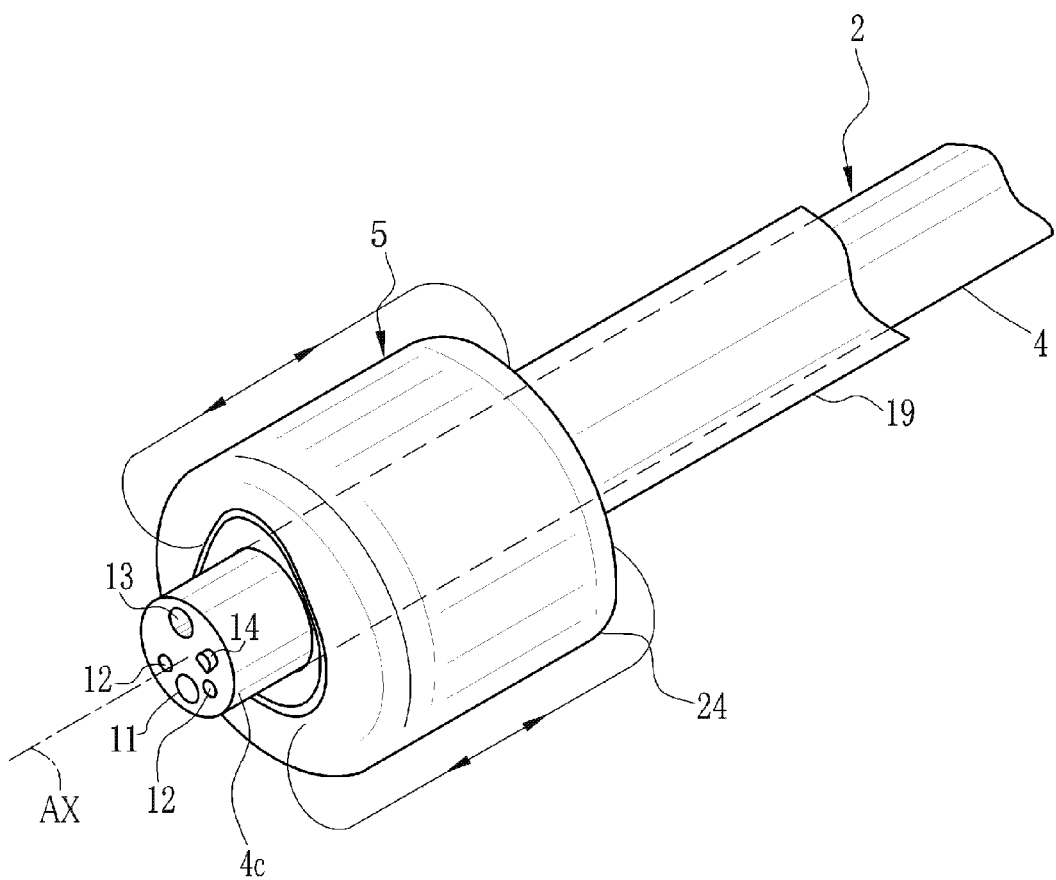
FIG. 2 is a perspective view showing a tip end portion of the endoscope and the propelling device.

As shown in FIG. 2, the tip end rigid portion 4c has an imaging window 11 provided at its front end surface. An objective optical system for imaging a part to be observed and a CCD or CMOS image sensor are built inside the imaging window 11. The image sensor is connected to the processor device via the manipulating part 3, the insertion part 4, and the signal cable passed through the universal cord 6.

The image of the part to be observed is formed on a light-receiving surface of the image sensor through the imaging window 11 and the objective optical system, and is converted into an image signal. The processor device performs various kinds of image processing on the image signal from the image sensor received via the signal cable, and then displays an observation image based on the image signal on a monitor (not shown).

Furthermore, the front end surface of the tip end rigid portion 4c is provided with an illumination window 12, a forceps outlet 13, and a jet nozzle 14, in addition to the imaging window 11. The illumination window 12 is configured to illuminate the part to be observed, and an illumination light from the light source device guided by the light guide is irradiated toward the part to be observed through the illumination window 12. The forceps outlet 13 exposes the front end of a treatment tool inserted through the forceps entrance 7. The jet nozzle 14 jets air or water, which is supplied from the air/water supply device disposed in the light source device, toward the imaging window 11 in response to manipulation of the air/water supply buttons.

The propelling device 5 is detachably mounted on the tip end side of the insertion part 4 extending from the curving portion 4b to the tip end rigid portion 4c. Furthermore, the mounting position of the propelling device 5 on the insertion part 4 may be changed appropriately. The propelling device 5 is driven by a driving source 16 such as a motor. The driving source 16 is coupled to a torque wire 17 that transmits the rotary torque for driving the propelling device 5. Furthermore, a torque coil may be used instead of the torque wire.

The torque wire 17 is passed through a protective sheath 18 and rotates inside the protective sheath 18. An elastic overtube 19 is externally fitted to the insertion part 4 in the direction of the insertion axis AX. The torque wire 17 in a state being covered with the protective sheath 18 is passed between the overtube 19 and the insertion part 4, and the tip end thereof reaches the propelling device 5.

A manipulation unit 21 is connected to the driving source 16. The manipulation unit 21 includes various buttons such as a button for inputting instructions for advancing, retreating, and stopping of the propelling device 5 and a speed adjustment button for adjusting the movement speed of the propelling device 5, and a control circuit for controlling driving of the driving source 16 in response to manipulation of the respective buttons.

Figure 3:
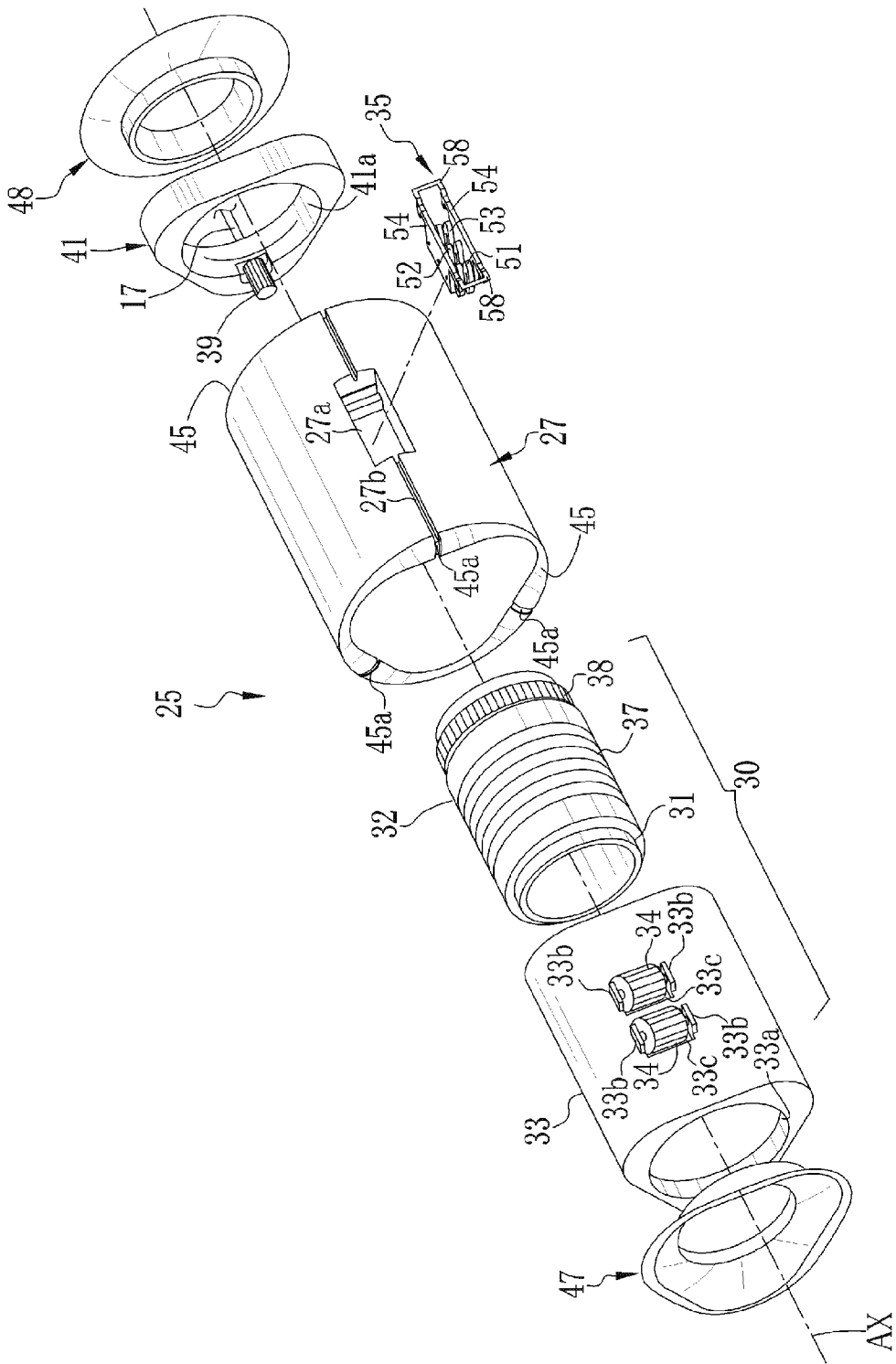
FIG. 3 is an exploded perspective view of the propelling device.
Figure 4:
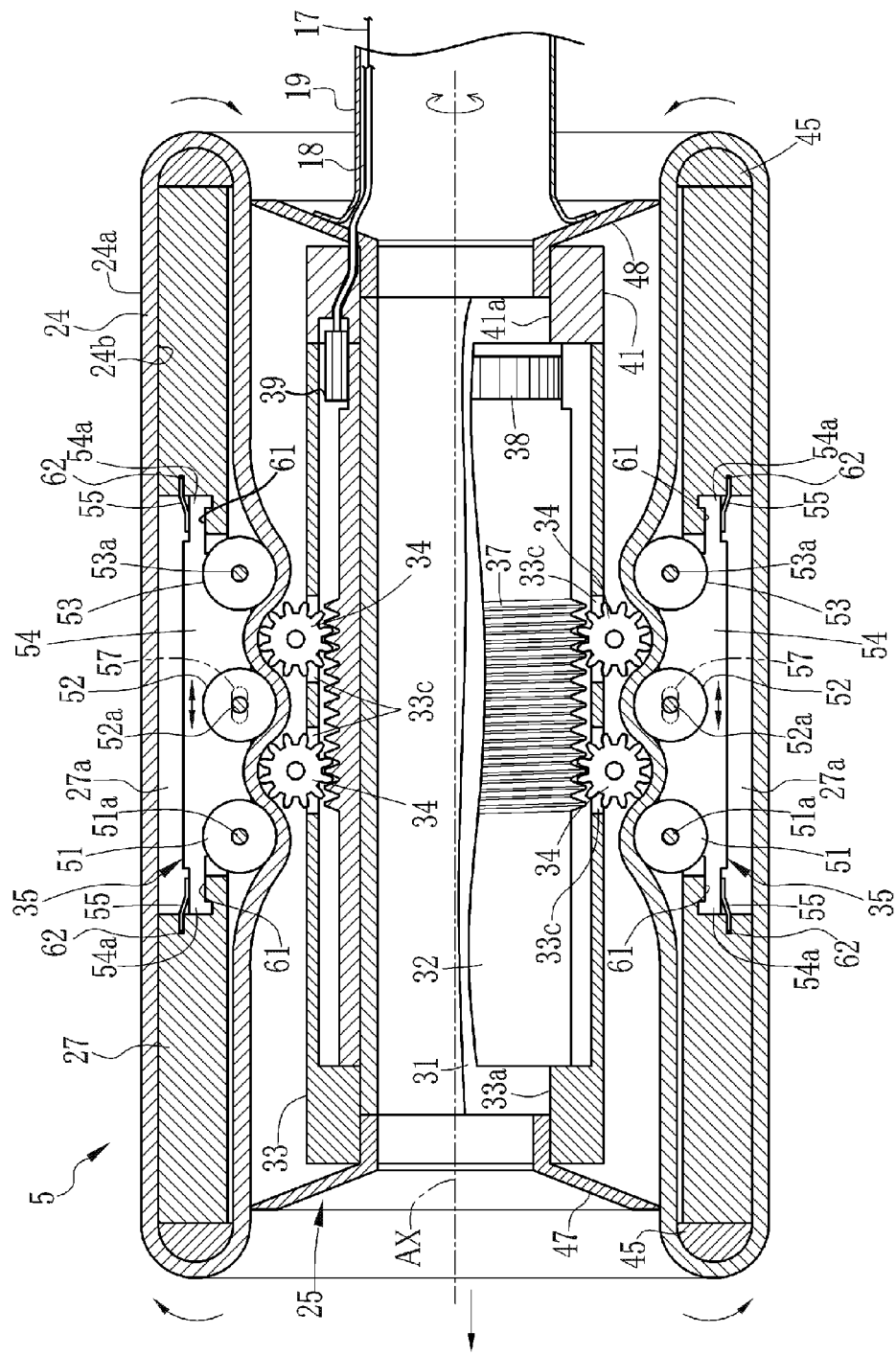
FIG. 4 is a cross-sectional view of the propelling device.
Figure 5:
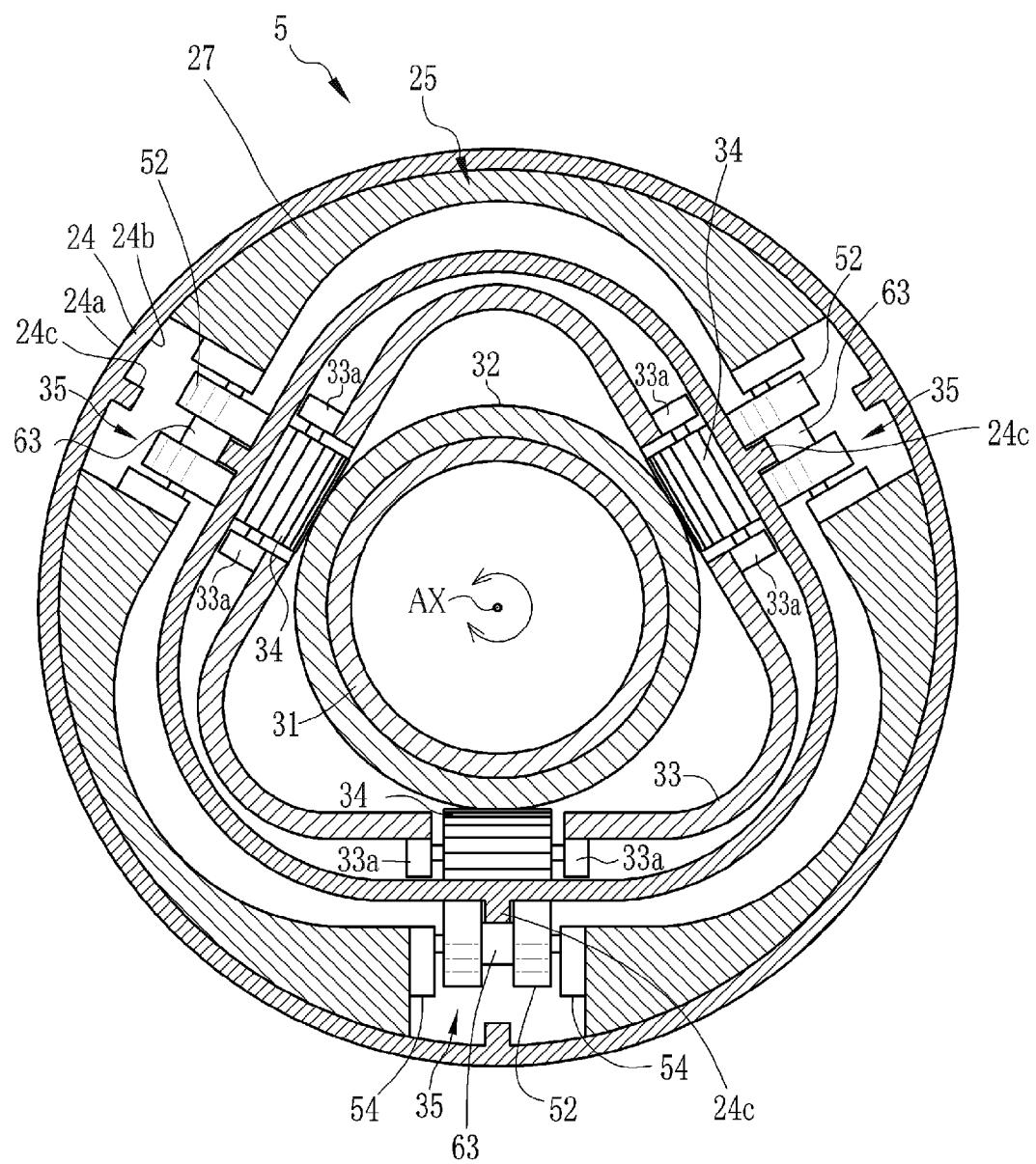
FIG. 5 is a cross-sectional view seen from the front of the propelling device.

In FIGS. 3 to 5, the propelling device 5 has a traveling body 24 that comes into contact with the inner wall surface of an alimentary canal or the like so as to make the insertion part 4 generate a propulsive force, and a driving mechanism 25. Furthermore, only the driving mechanism 25 is illustrated in FIG. 3. FIG. 4 is a cross-sectional view obtained by longitudinally dividing the propelling device 5 at intervals of 120 degrees.

The traveling body 24 is referred to as "toroid" in JP 2009-513250 A, for example, and is a hollow annular body in the shape of a doughnut. An external cylinder 27 is arranged in the hollow interior of the traveling body 24. As for the traveling body 24, a sheet is rounded to form a tube, and the tube is folded back from the middle thereof so as to encompass the external cylinder 27 in a state where the tube is passed through the interior of the external cylinder 27. After the folding-back of the tube, both ends of the tube are adhered with each other by heat welding or the like. As the sheet for forming the traveling body 24, for example, biocompatible plastics having flexibility, such as polyvinyl chloride, polyamide resin, fluororesin, urethane, and polyurethane, are used.

The portion of the traveling body 24 outside the external cylinder 27 and the portion thereof inside the external cylinder 27 move in mutually opposite directions along the insertion axis AX, and thereby the traveling body 24 travels in a circulating manner such that the traveling body 24 moves from the inside of the external cylinder 27 to the outside thereof and returns to the inside again. The outer surface 24a of the traveling body 24 comes into contact with the inner wall of a tract within the body at the outside of the external cylinder 27. Thereby, a propulsive force for advancing or retreating the insertion part 4 in the direction along the insertion axis AX is generated. The direction of the propulsive force is a direction in which the insertion part 4 is moved, and is a direction opposite to the movement direction of the traveling body 24 outside the external cylinder 27.

The driving mechanism 25 has a function of mounting the propelling device 5 on the endoscope 2, and a function of making the traveling body 24 travels in a circulating manner. The driving mechanism 25 is constituted by a mounting cylinder 31, a rotation cylinder 32, and a housing cylinder 33 that constitute an inner unit 30, two driving gears 34, a roller unit 35, and the like, in addition to the external cylinder 27.

The mounting cylinder 31 has a cylindrical shape of which internal diameter is almost equal to that of the tip end rigid portion 4c, and fits into the tip end side of the insertion part 4. This allows the insertion part 4 to be mounted on the propelling device 5. The rotation cylinder 32 is formed in a cylindrical shape having an approximately the same internal diameter as the external diameter of the mounting cylinder 31, and rotatably fitted into the outer periphery of the mounting cylinder 31, so as to rotate around the insertion axis AX. The length of the rotation cylinder 32 (the length thereof in the direction of the insertion axis AX) is shorter than that of the mounting cylinder 31, and the mounting cylinder 31 protrudes from the front and rear ends of the rotation cylinder 32.

The outer peripheral surface of the rotation cylinder 32 is provided with a spiral worm gear 37 having the insertion axis AX as a central axis, and a spur gear 38 arranged in the circumferential direction. A pinion gear 39 provided at the front end of the torque wire 17 meshes with the spur gear 38. Thereby, in accordance with the rotation of the driving source 16, the rotation cylinder 32 rotates.

The housing cylinder 33 has a substantially triangular cross-section (a shape such that respective angles of the equilateral triangle are rounded), and accommodates the mounting cylinder 31 and the rotation cylinder 32 therein. The front surface of the housing cylinder 33 has a circular opening 33a, and the internal diameter of the circular opening 33a is the same as the external diameter of the mounting cylinder 31. The front end portion of the mounting cylinder 31 is fitted into the opening 33a. Additionally, a lid 41 is fixed to the rear end of the housing cylinder 33. The outline of the lid 41 is substantially triangular, and has the same shape as that of the housing cylinder 33. The lid cylinder 41 has an opening 41a, and the internal diameter of the opening 41a is the same as the external diameter of the mounting cylinder 31. The rear end portion of the mounting cylinder 31 is fitted into the opening 41a. Thereby, the mounting cylinder 31 and the rotation cylinder 32 are accommodated in the housing cylinder 33. Furthermore, the torque wire 17 is guided into the housing cylinder 33 through a hole (not shown) formed in the lid 41.

Two sets of attachment ribs 33b are formed in each of three planar portions of the housing cylinder 33. The driving gear 34 is rotatably attached to each of the sets of the attachment ribs 33b. The driving gears 34 are disposed side by side in the direction of the insertion axis AX that is a direction in which the traveling body 24 is made to travel, and the direction of the insertion axis AX is a gear arrangement direction. Additionally, the rotating shafts of the driving gears 34 are parallel to each other, and are made orthogonal to the insertion axis AX. Furthermore, when the two driving gears 34 are distinguished from each other in the following description, the driving gear 34 at the front end of the propelling device 5 is referred to as a front driving gear 34, and the driving gear 34 at the rear end of the propelling device 5 is referred to as a rear driving gear 34.

Two openings 33c are formed in each of the three planar portions of the housing cylinder 33. Each of the driving gears 34 is partially exposed to the inside of the housing cylinder 33 through the respective openings 33c, and mesh with the worm gear 37. Thereby, when the rotation cylinder 32 rotates around the insertion axis AX, the respective driving gears 34 rotate. Accordingly, the driving gear 34 is a worm wheel, and the teeth height of the driving gear 34 is low so as not to damage the traveling body 24.

The cross-sectional shape of the external cylinder 27 in the direction orthogonal to the insertion axis AX is a circular shape at the outer peripheral surface thereof. The shape of the inside of the external cylinder 27 is almost the same triangular shape as that of the housing cylinder 33, but is larger than the outer shape of the housing cylinder 33, and the housing cylinder 33 that holds the mounting cylinder 31 and the rotation cylinder 32 is accommodated in the external cylinder 27. As mentioned above, the traveling body 24 is wound around the external cylinder 27. Sliding members 45 that slide on an inner surface 24b of the traveling body 24 are attached to the front and rear ends of the external cylinder 27, respectively. Each of the sliding members 45 has a low coefficient of friction at the surface thereof, and is adapted such that the traveling body 24 travels in a circulating manner smoothly.

A front stopper 47 is attached to the front end of the housing cylinder 33, and a rear stopper 48 is attached to the rear end of the lid 41. Each of the stoppers 47 and 48 has a conical shape that opens toward the outside, and block an opening between the traveling body 24 and the housing cylinder 33, to prevent the inner wall of an alimentary canal from entering the interior of the propelling device 5 in accordance with the circulation-travel of the traveling body 24.

In three planar portions of the inner peripheral surface of the external cylinder 27, openings 27a that penetrate the wall surface of the external cylinder 27 are formed in the portions that face the driving gears 34, respectively. A roller unit 35 is attached to each of the openings 27a. The roller unit 35 is constituted by unitizing three driven rollers 51 to 53. The roller unit 35 pushes the traveling body 24 toward the driving gears 34, and pinches the traveling body 24 between the driven rollers 51 to 53 and the driving gears 43 such that the traveling body 24 travels in a circulating manner.

Furthermore, the roller unit 35 is attached to the external cylinder 27 before the traveling body 24 is mounted on the external cylinder 27. The locations where the roller units 35 are attached are not limited to three, and the number of the roller units may be appropriately changed.

Figure 6:
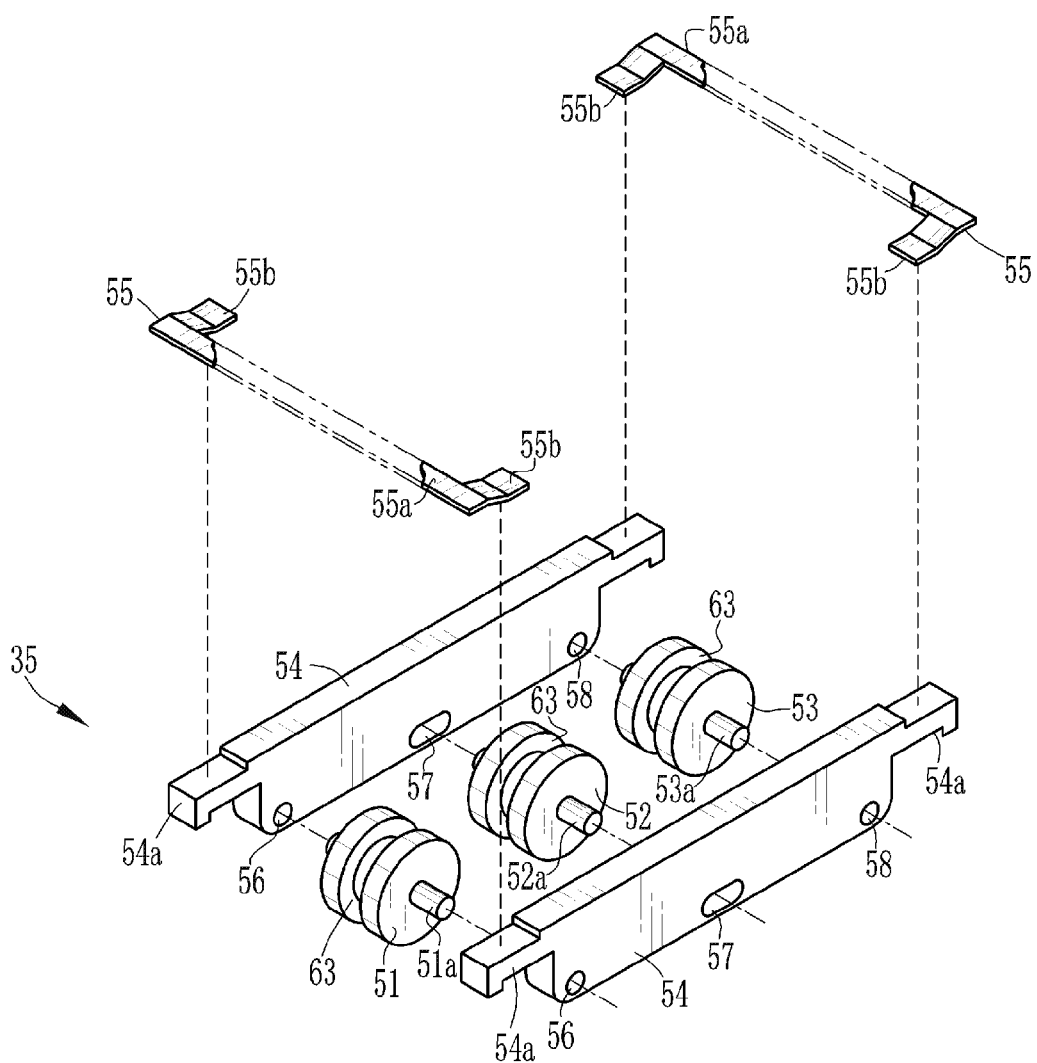
FIG. 6 is an exploded perspective view of a roller unit.

As shown in FIG. 6, each of the roller units 35 has the driven rollers 51 to 53, a pair of holding members 54 for rotatably holding the driven rollers 51 to 53 so as to be spaced out with each other in the gear arrangement direction, and a pair of flat springs 55 as attachment members.

The traveling body 24 is pinched between the driven rollers 51 to 53 and the driving gears 34 such that the rotation of each of the driving gears 34 is transmitted to the traveling body 24. The driven rollers 51 to 53 are rotatably held by rotating shafts 51a to 53a, respectively.

Each of the holding members 54 has shaft holes 56 to 58. Each end of the rotating shaft 51a of the driven roller 51 is fixed to and held by the pair of shaft holes 56, and each end of the rotating shaft 53a of the driven roller 53 is fixed to and held by the pair of shaft holes 58. The shaft hole 57 is formed between the shaft hole 56 and the shaft hole 58. The shaft hole 57 is a long hole that is made long in the direction of the insertion axis AX, that is, in the gear arrangement direction. As each end of the rotating shaft 52a is held by the pair of shaft holes 57 that are formed as the long holes, the driven roller 52 is made to be movable in the gear arrangement direction. Here, the driven roller 52 is the first driven roller, and the shaft holes 57 are the first shaft holes. Additionally, the driven rollers 51 and 53 are the second driven rollers, and the shaft holes 56 and 58 are the second shaft holes.

As shown in FIG. 4, each end portion 54a of the holding member 54 is engaged with corresponding stepped portions 61 formed inside the opening 27a of the external cylinder 27, and the roller unit 35 is disposed inside the opening 27a. The direction in which the driven rollers 51 to 53 are disposed side by side is made to coincide with the direction in which the driving gears 43a and 43b are disposed side by side (the gear arrangement direction), and the rotating shafts 51a to 53a are made parallel to the rotating shafts of the driving gears 34. Furthermore, in FIG. 4, the illustration of the holding member 54 on the near side of the drawing is omitted.

As shown in FIG. 6, each of the flat springs 55 is formed substantially in the shape of a channel in which respective end portions 55b are bent with respect to a central portion 55a. The flat spring 55 is fixed in a state that the central portion 55a is fitted into slits 62 formed in inner wall surfaces above the stepped portions 61, and biases the top faces of the end portions 54a of the holding members 54 toward the inside of the external cylinder 27 with the end portions 55b. This allows one or both of the end portions 54a of the roller unit 35 to move to the outside of the external cylinder 27 against the biasing of the flat spring 55. In a case where only one of the end portions 54a of the roller unit 35 moves, or in a case where there is a difference in the movement distances of the end portions 54a, the rotation of the roller unit 35 around an axis parallel to the rotating shafts 51a to 53a is allowed.

In a state where the roller unit 35 is assembled in the opening 27a as mentioned above, each of the driven rollers 51 to 53 protrudes into the inside of the external cylinder 27, and while the traveling body 24 is wound around the driving gears 34, the traveling body 24 is pinched between the driven rollers 51 to 53 and the driving gears 34. The rotating shaft 51a of the driven roller 51 is disposed at a position closer to the front end of the propelling device 5 than the rotating shaft of the front driving gear 34, such that the traveling body 24 is pinched between the driven roller 51 and the front end portion of the front driving gear 34. The rotating shaft 53a of the driven roller 53 is disposed at a position closer to the rear end of the propelling device 5 than the rotating shaft of the rear driving gear 34, such that the traveling body 24 is pinched between the driven roller 53 and the rear end portion of the rear driving gear 34.

The driven roller 52 is disposed so as to face a portion between the front driving gear 34 and the rear driving gear 34 by positioning the shaft hole 57 almost at the center between the rotating shafts of the driving gears 34. Thereby, the driven roller 52 pinches the traveling body 24 between the driven roller 52 and the front driving gear 34, and simultaneously pinches the traveling body 24 between the driven roller 52 and the rear driving gear 34.

Since the roller unit 35 is rotatable around the axis vertical or parallel to the rotating shafts 51a to 53a, automatic positioning is made so that the pinching force between the driven roller 51 and the front driving gear 34 and the pinching force between the driven roller 53 and the rear driving gear 34 become uniform. On the other hand, the positional relationships between the driven roller 51 and the front driving gear 34 and between the driven roller 53 and the rear driving gear 34 are respectively determined. If the positional relationships between the driven rollers 51, 53 and each of the driving gears 34 are determined, the positional relationships of the driven roller 52 with respect to the respective driving gears 34 are also determined in a case where the position of the driven roller 52 is fixed completely. Therefore, the pinching forces between the driven roller 52 and the respective driving gears 34 are apt to become non-uniform. Additionally, as one of the causes of the pinching forces becoming non-uniform, there is a variation in the assembling position of the driven rollers 51 to 53 or the driving gears 34.

However, since the driven roller 52 is made movable in the gear arrangement direction by making the shaft hole 57 as a long hole as mentioned above, the driven roller 52 moves to and is positioned at a position where the gap between the driven roller 52 and the front driving gear 34 and the gap between the driven roller 52 and the rear driving gear 34 become uniform. Thereby, the pinching forces that pinch the traveling body 24 between the driven roller 52 and the respective driving gears 34 are made uniform.

As shown in FIG. 5, the inner surface 24b of the traveling body 24 is formed with three linear projections 24c. The linear projections 24c are formed along the circulation direction of the traveling body 24 over the entire circumference. Additionally, as shown in FIGS. 5 and 6, grooves 63 into which the linear projections 24c fit on a one-to-one basis are formed along the circumferential direction, and each of the grooves 63 is located at the central portion of corresponding one of the driven rollers 51 to 53. Furthermore, in FIG. 5, only the driven roller 52 of the driven rollers 51 to 53 is drawn. Moreover, as shown in FIG. 3, the external cylinder 27 and the sliding member 45 are formed with grooves 27b and 45a respectively into which each of the linear projections 24c fits.

As the traveling body 24 travels in a state where the linear projections 24c fit into the groove portions 27b, 45a, and 63, the traveling body 24 is prevented from rotating in the circumferential direction of the external cylinder 27. Additionally, as the linear projections 24C fit into the grooves 63, the rotating shaft 52a of the driven roller 52 is prevented from inclining with respect to the rotating shaft of the driving gear 34.

Next, the operation of the above configuration will be described. The overtube 19 is attached to the insertion part 4 of the endoscope 2, and the mounting cylinder 31 is fitted into the tip end rigid portion 4c, so as to attach the propelling device 5 to the tip end side of the insertion part 4. After the attachment of the overtube 19 and the propelling device 5, the power sources of the processor device, the light source device, the manipulation unit 21, and the like are turned on. Then, the insertion part 3 of the endoscope 2 is inserted into an alimentary canal, for example, the large intestine of a patient. Furthermore, as a method of attaching the propelling device 5 to the tip end side, for example, a collet described in JP 2009-513250 A or the like can be used.

After the tip end rigid portion 4c is inserted into a predetermined position of the large intestine, for example, a position immediately before the sigmoid colon, the manipulation unit 21 is manipulated to input an instruction indicating advance. If the instruction indicating advance is input, the rotation generated in the driving source 16 is transmitted to the pinion gear 39 via the torque wire 17. Thereby, the rotation cylinder 32 formed with the spur gear 38 that meshes with the pinion gear 39 rotates.

If the worm gear 37 rotates in accordance with the rotation of the rotation cylinder 32, the respective driving gears 34 that mesh with the worm gear 37 rotate. The rotation of the respective driving gears 34 is transmitted to the traveling body 24 pinched between the respective driving gears 34 and the respective driven rollers 51 to 53 as a driving force, and the traveling body 24 travels in the direction shown by the arrow of FIG. 4. That is, the traveling body 24 moves from the rear end of the propelling device 5 toward the front end thereof at the outside of the external cylinder 27, and moves from the front end of the propelling device 5 toward the rear end thereof at the inside of the external cylinder 27, and thus, the traveling body 24 travels in a circulating manner.

Since the outer surface 24a of the traveling body 24 comes into contact with the inner wall of the large intestine, the tip end rigid portion 4c moves forward along a tract within the body by the reaction force of the force that draws in the inner wall of the large intestine from the front side and sends it to the rear side with the circulation-travel of the traveling body 24.

If a speed change is instructed by the manipulation of the manipulation unit 21, the rotating speed of the torque wire 17 by the driving source 16 is changed. As a result, the rotating speed of each of the driving gears 34 is changed, and the speed of the traveling body 24 varies. This increases or decreases the advancing speed of the insertion part 4. If retreat is instructed by the manipulation of the manipulation unit 21, the torque wire 17 is reversely rotated by the driving source 16, and the rotational direction of each of the driving gears 34 also becomes the opposite direction. Thereby, the circulation direction of the traveling body 24 becomes a direction opposite to the direction at the time of advancing, and as a result, the insertion part 4 is retreated. Moreover, if stopping is instructed by the manipulation of the manipulation unit 21, the driving source 16 is stopped and the propelling device 5 stops. By appropriately performing the above manipulations, the tip end rigid portion 4c can be moved to a desired part within the large intestine.

By the way, as described above, the traveling body 24 is pinched between the respective driving gears 34 and the respective driven rollers 51 to 53, and thereby the rotation of the driving gears 34 is transmitted to the traveling body 24 as a driving force, and the traveling body 24 travels. If the pinching forces between the respective driving gears 43a and 43b and the respective driven rollers 51 to 53 are non-uniform, not only a driving force is no longer transmitted to the traveling body 24 effectively, but also tensioning or loosening occurs on the traveling body between the respective driving gears, which causes damage to the traveling body 24, the driving gears 34, and the driven rollers 51 to 53.

However, as the rotation of the roller unit 35 is allowed, the pinching force between the driven roller 51 and the front driving gear 34 and the pinching force between the driven roller 53 and the rear driving gear 34 are made uniform, and the respective pinching forces between the driven roller 52 and the front driving gear 34 and between the driven roller 52 and the rear driving gear 34 are also made uniform by the movement of the driven roller 52 in the gear arrangement direction. Accordingly, a driving force is effectively transmitted to the traveling body 24 from the respective driving gears 34, and the tensioning or loosening of the traveling body 24 that causes damage to the traveling body 24, the driving gears 34, the driven rollers 51 to 53, and the like does not occur.

Figure 7:
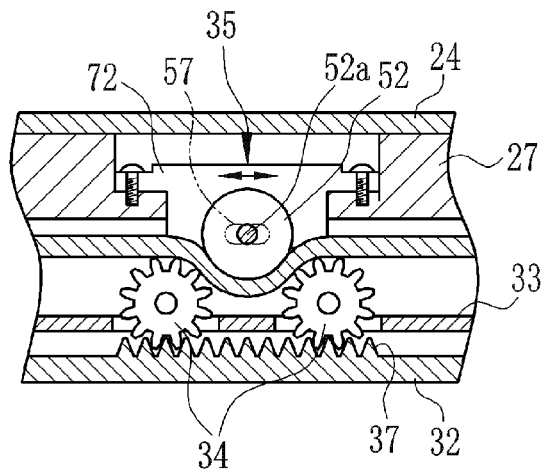
FIG. 7 is a partial cross-sectional view showing a propelling device provided with one driven roller.

In the above embodiment, a configuration in which one first driven roller and two second driven rollers are used with respect to two driving gears is adopted. Instead of this, for example as shown in FIG. 7, a configuration in which one driven roller 52 is used with respect to two driving gears 34 may be adopted. Since the embodiment shown in FIG. 7 has the same configuration as the first embodiment except that one driven roller is used and the roller unit 35 is fixed to the external cylinder 27, the same constituent parts in terms of function and configuration are designated by the same reference numerals and the description thereof is omitted. Furthermore, in FIG. 7, the illustration of a holding member 72 on the near side of the drawing is omitted.

In the embodiment shown in FIG. 7, each end of the rotating shaft 52a of the driven roller 52 is held by oblong shaft holes 57 formed in a pair of the holding members 72, and thereby the driven roller 52 is made movable in the gear arrangement direction. Each end of each of the holding members 72 is screwed to the external cylinder 27 to fix the roller unit 35 to the external cylinder 27.

In a case where the roller unit 35 is fixed as described above, due to a variation in the fixing position thereof, a variation in the assembling position of the driven roller 52 or the driving gear 34, or the like, the respective gaps between the driven roller 52 and the respective driving gears 34 may become non-uniform, and thus, the respective pinching forces may become non-uniform. However, by virtue of the configuration in which the driven roller 52 is made movable in the gear arrangement direction, the driven roller 52 by itself moves to and is positioned at a position where the respective gaps between the driven roller 52 and the respective driving gears 34 become uniform, and the pinching forces of the respective driving gears 34 are made uniform.

Although there is used only one first driven roller, two or more first driven rollers may be used. The driven roller which is disposed to face a portion between a pair of adjacent driving gears may be used as the first driven roller. It is also preferable that N is two or more, N number of driving gears are used, the first driven roller is disposed so as to face the portion between the N number of driving gears, respectively, such that the traveling body is pinched between the driven roller and each of a pair of the adjacent driving gears. In this case, (N−1) number of driven rollers are held so as to be movable in the gear arrangement direction as the first driven rollers. Additionally, the second driven rollers may be provided at each end in the gear arrangement direction such that the second driven rollers sandwich (N−1) number of the first driven rollers in the gear arrangement direction. Furthermore, in the embodiment shown first, N is two.

Figure 8:
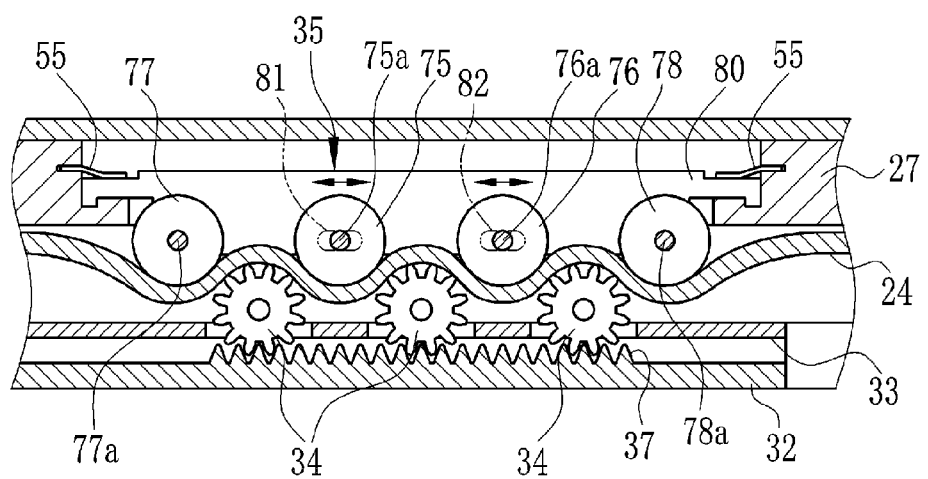
FIG. 8 is a partial cross-sectional view showing a propelling device provided with four driven rollers.

According to the embodiment shown in FIG. 8, there are provided three driving gears 34 (N=3), driven rollers 75 and 76 which are two first driven rollers (N−1=2), and driven rollers 77 and 78 which are two second driven rollers. Both ends of the rotating shafts 75a to 78a of the driven rollers 75 to 78 are held by shaft holes formed in holding members 80. The rotating shafts 75a and 76a of the driven rollers 75 and 76 are held by shaft holes 81 and 82 that are made long in the gear arrangement direction, and thereby the driven rollers 75 and 76 are made movable in the gear arrangement direction. The rotating shafts 77a and 78a of the driven rollers 77 and 78 are fixed to the holding members 80.

Figure 9:
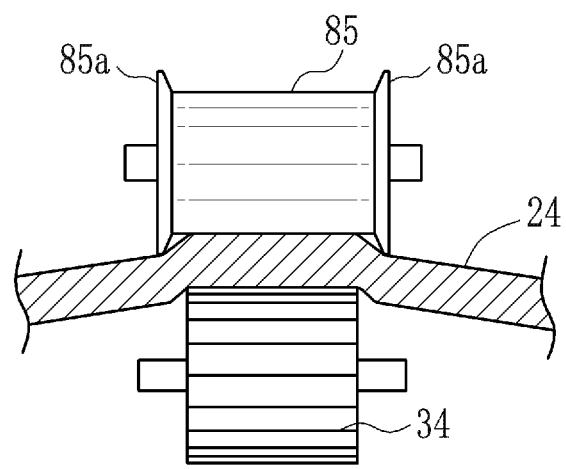
FIG. 9 is a schematic view showing a driven roller having a flange.

In the above respective embodiments, the linear projection is continuously formed over the entire circumference of the traveling body. However, a plurality of projections may be formed at intervals. Instead of the configuration in which the linear projection is fitted into the groove provided in the driven roller, as shown in FIG. 9, flanges 85a may be provided at each end of a driven roller 85. Furthermore, a configuration may be adopted in which a flange is provided at each end of a driven roller and the linear projection of the traveling body fits into a groove provided in the driven roller.

Figure 10:
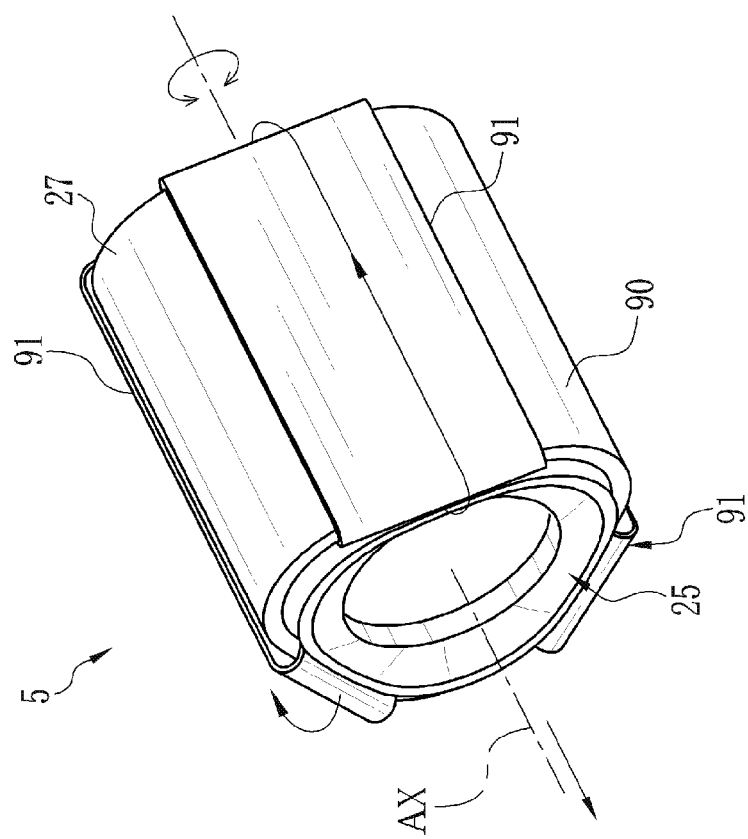
FIG. 10 is a perspective view showing a propelling device having an endless belt.

The traveling body is in the shape of a tubular bag that covers the external cylinder over the entire circumference. However, as shown in FIG. 10, a plurality of endless belts 91 each of which covers a part of the external cylinder 90 in the circumferential direction may be used. In the embodiment shown in FIG. 10, the external cylinder 90 has a tubular shape of which the cross-section is substantially triangular.

In the above embodiments, the present invention is applied to an endoscope insertion assisting device for assisting insertion and extraction of an endoscope by advancing and retreating it. However, the present invention also can be applied to an endoscope insertion assisting device for assisting any one of advancing and retreating of an endoscope.

In the above embodiments, the shape of the outer peripheral surface of the external cylinder is circular or triangle. However, in addition to this, polygonal shapes such as a quadrangle may be adopted.

The present invention also can be applied to other endoscopes and probes for industrial use or the like other than the endoscope for medical diagnosis. In the present invention, various alterations and modifications can be made without departing from the spirit of the present invention and such alterations and modifications should also be interpreted as being included in the scope of protection of the present invention.

What is claimed is:

1. A propelling device that is mounted on an insertion part of an endoscope and receives a driving force from a driving source to propel the insertion part within a tract, comprising:
   a mounting cylinder that fits into the insertion part;
   an external cylinder disposed at an outer periphery of the mounting cylinder;
   a traveling body that moves from an inside of the external cylinder to an outside thereof and returns to the inside again so as to travel in a circulating manner, the traveling body being wound around the external cylinder so as to be made endless;
   at least two driving gears that rotate by receiving the driving force from the driving source, the two driving gears being disposed closer to the mounting cylinder than the traveling body inside the external cylinder, and the two driving gears being disposed side by side with rotating shafts thereof parallel to each other in a direction in which the traveling body is made to travel;
   a first driven roller that is rotatably provided to the external cylinder so as to face a portion between the two driving gears, the first driven roller having a rotating shaft parallel to the rotating shafts of the driving gears, and the first driven roller pinching the traveling body between the first driven roller and the respective driving gears so as to transmit the rotation of the respective driving gears to the traveling body; and
   one set of first shaft holes for holding each end of the rotating shaft of the first driven roller, each of the first shaft holes being formed to be long in a gear arrangement direction in which the driving gears are disposed side by side, such that the first driven roller is held by the first shaft holes so as to be movable in the gear arrangement direction.

2. The propelling device according to claim 1, further comprising two second driven rollers disposed side by side in the gear arrangement direction so as to sandwich the first driven roller, such that each of the second driven rollers and each of the driving gears pinch the traveling body therebetween.

3. The propelling device according to claim 2, further comprising a roller unit, wherein the roller unit includes:
   said first driven roller and said second driven rollers;
   a pair of holding members which is disposed at each side of the first driven roller and the second driven rollers, each of the holding members being formed with the first shaft hole and second shaft holes for holding ends of the rotating shafts of the two second driven rollers; and
   an attachment member for holding the holding member at the external cylinder such that the holding member is rotatable around a rotating shaft parallel to the first driven roller.

4. The propelling device according to claim 1, further comprising:
- a rotation cylinder rotatably disposed at the outer periphery of the mounting cylinder, the rotation cylinder being rotated by receiving the driving force from the driving source;
- a worm gear formed at an outer peripheral surface of the rotation cylinder, the worm gear meshing with the driving gears, such that the driving gears are rotated by the rotation of the rotation cylinder; and
- a housing cylinder disposed between the rotation cylinder and the external cylinder and provided with said driving gears protruding from an outer peripheral surface thereof.

5. The propelling device according to claim 1, wherein the traveling body is a tubular bag.

6. The propelling device according to claim 1, wherein the traveling body is constituted of a plurality of endless belts.

7. A propelling device that is mounted on an insertion part of an endoscope and receives a driving force from a driving source to propel the insertion part within a tract, comprising:
- a mounting cylinder that fits into the insertion part;
- an external cylinder disposed at an outer periphery of the mounting cylinder;
- a traveling body that moves from an inside of the external cylinder to an outside thereof and returns to the inside again so as to travel in a circulating manner, the traveling body being wound around the external cylinder so as to be made endless;
- N (N is two or more) number of driving gears that rotate by receiving the driving force from the driving source, the N number of the driving gears being disposed closer to the mounting cylinder than the traveling body inside the external cylinder, and the N number of the driving gears being disposed side by side with rotating shafts thereof parallel to each other in a direction in which the traveling body is made to travel;
- (N−1) number of first driven rollers rotatably provided at the external cylinder, each of the (N−1) number of the first driven rollers being disposed to face a portion between the adjoining driving gears, each of the (N=1) number of the first driven rollers having a rotating shaft made parallel to the rotating shafts of the driving gears, and each of the (N−1) number of the first driven rollers and each of the driving gears pinching the traveling body therebetween to transmit the rotation of each of the driving gears to the traveling body; and
- (N−1) number of sets of first shaft holes for holding each end of the rotating shafts of the (N−1) number of the first driven rollers, the (N−1) number of sets of the first shaft holes being formed to be long in a gear arrangement direction in which the driving gears are disposed side by side, such that the (N−1) number of the first driven rollers are held by the (N−1) number of sets of the first shaft holes so as to be movable in the gear arrangement direction.

8. The propelling device according to claim 7, further comprising two second driven rollers disposed at each end in the gear arrangement direction so as to sandwich the (N−1) number of the first driven rollers, each of the second driven rollers and each of the driving gears pinching the traveling body therebetween.

9. The propelling device according to claim 8, wherein the traveling body is a tubular bag.

10. The propelling device according to claim 8, wherein the traveling body is constituted of a plurality of endless belts.

* * * * *